United States Patent
Knowlton

(10) Patent No.: US 11,862,343 B2
(45) Date of Patent: *Jan. 2, 2024

(54) MEDICATION RISK MITIGATION SYSTEM AND METHOD

(71) Applicant: CareKinesis, Inc., Moorestown, NJ (US)

(72) Inventor: Calvin H. Knowlton, Moorestown, NJ (US)

(73) Assignee: CAREKINESIS, INC., Moorestown, NJ (US)

( * ) Notice: Subject to any disclaimer, the term of this patent is extended or adjusted under 35 U.S.C. 154(b) by 469 days.

This patent is subject to a terminal disclaimer.

(21) Appl. No.: 16/928,557

(22) Filed: Jul. 14, 2020

(65) Prior Publication Data

US 2020/0342995 A1    Oct. 29, 2020

Related U.S. Application Data

(63) Continuation of application No. 14/579,283, filed on Dec. 22, 2014, now Pat. No. 10,720,241.

(60) Provisional application No. 61/920,052, filed on Dec. 23, 2013.

(51) Int. Cl.
*G16H 50/30* (2018.01)
*G16H 20/10* (2018.01)
*G16H 40/67* (2018.01)
*G16H 10/60* (2018.01)

(52) U.S. Cl.
CPC ............. *G16H 50/30* (2018.01); *G16H 20/10* (2018.01); *G16H 40/67* (2018.01); *G16H 10/60* (2018.01)

(58) Field of Classification Search
CPC ........ G16H 50/30; G16H 20/10; G16H 40/67; G16H 10/60; G06F 19/3431; G06F 19/3456; G06F 19/322
See application file for complete search history.

(56) References Cited

U.S. PATENT DOCUMENTS

| | | | |
|---|---|---|---|
| 8,170,890 B1 * | 5/2012 | Lawlor | G16H 20/10 600/300 |
| 8,392,220 B2 | 3/2013 | Knowlton et al. | |
| 8,700,430 B2 | 4/2014 | Miller et al. | |
| 8,719,055 B2 | 5/2014 | Huser et al. | |
| 2002/0029223 A1 | 3/2002 | Rice et al. | |
| 2002/0143579 A1 | 10/2002 | Docherty et al. | |

(Continued)

*Primary Examiner* — Peter H Choi
*Assistant Examiner* — Chad A Newton
(74) *Attorney, Agent, or Firm* — Morgan, Lewis & Bockius LLP

(57) ABSTRACT

A medication risk mitigation method utilizing three interventions: a prospective intervention performed by a prescriber, a concurrent intervention performed by a pharmacist and a retroactive intervention performed by a pharmacist. At each intervention, the system of the instant invention utilizes a computer program to compare each prescribed medication to a series of intrinsic and extrinsic data sources in order to identify potential contraindications and, if necessary, modify a prescription. The system also permits secure messaging between prescribers and pharmacists, each with access to the computer program, so as to facilitate communication and reduce medication risks. The system of this invention also permits modeling for hypothetical medication modifications based on the same intrinsic and extrinsic data sources.

4 Claims, 4 Drawing Sheets

(56) References Cited

U.S. PATENT DOCUMENTS

| | | | |
|---|---|---|---|
| 2003/0050802 A1* | 3/2003 | Jay | G16H 10/60 |
| | | | 705/3 |
| 2009/0254372 A1 | 10/2009 | Bartholomew et al. | |
| 2010/0198948 A1* | 8/2010 | Yang | G06F 9/5055 |
| | | | 709/222 |
| 2012/0303388 A1* | 11/2012 | Vishnubhatla | G06V 20/66 |
| | | | 705/2 |
| 2013/0179181 A1 | 7/2013 | Jackson et al. | |
| 2013/0274669 A1* | 10/2013 | Stempfle | A61M 5/1456 |
| | | | 604/151 |
| 2014/0229191 A1 | 8/2014 | Ryan et al. | |
| 2014/0316815 A1* | 10/2014 | Chen | G16H 10/20 |
| | | | 705/3 |
| 2016/0357929 A1* | 12/2016 | Ghouri | G16H 50/30 |

* cited by examiner

MEDICATION RISK MITIGATION SYSTEM AND METHOD

CROSS REFERENCE TO RELATED APPLICATION(S)

This application is a continuation of U.S. patent application Ser. No. 14/579,283, filed Dec. 22, 2014, which claims the benefit of U.S. Provisional Application No. 61/920,052, filed Dec. 23, 2013, each of which is incorporated by reference in its entirety.

FIELD OF THE INVENTION

The present invention relates in general to computer implemented medication risk management and, more specifically, reducing the likelihood of patient harm arising from prescribed medications.

BACKGROUND OF THE INVENTION

Patients routinely take one or more prescribed medications to treat illnesses. The pandemic of medication-related morbidity and mortality and the increasing rate and cost of medication-induced injuries is also well known in the art. Patients and society are burdened by emergency room visits and hospitalizations that often result from misadventures with prescription medications. Fortunately, disparate data sources provide useful insights into the interactions between two or more medications. Other data sources, referred to herein as intrinsic components, include personalized information related to a patient, such as patient lab test results, patient genetics, and a particular individual's history of adherence to prescription dosage schedules. Other data sources, referred to herein as extrinsic components, include information related to FDA warnings, Beers listed medications, and other non-patient specific information about a particular drug.

Currently, prescribers and pharmacists are unable to combine intrinsic and extrinsic components in a way that provides meaningful interventions with adequate procedures in place to avoid not only harmful interactions between two or more drugs, but also see potential harms related to other intrinsic components that may be patient-specific. There exists a further need in the art to integrate medication decision support with an internet-driven platform used by both prescribers and pharmacists.

SUMMARY OF THE INVENTION

According to the present invention, the foregoing and other objects and advantages are obtained by using a method for mitigating medication risk, comprising a network linked computer program product further comprising a non-transitory computer readable medium having program instructions stored in a memory device, the instructions executable by a processor to direct the performance of operations for the management of a regimen for a patient's use of prescribed medication. The program instructions comprise the steps of initializing a prospective intervention, a concurrent intervention and a retrospective intervention. The prospective intervention comprises the steps of receiving at least one medication input from a prescriber for a patient into the memory device; comparing the at least one medication input for the patient to at least one intrinsic component data source or extrinsic component data source; sending a first message to the prescriber through a network linked system if the at least one medication input is matched with at least one contraindication based on the comparison between the at least one medication input and the at least one intrinsic component data source or extrinsic component data source; and editing the at least one medication input with any modifications the prescriber may make based on the contraindication, thereby creating one or more prescribed medications. The concurrent intervention comprises the steps of sending a second message to a pharmacist through the network linked system comprising the one or more prescribed medications; comparing the one or more prescribed medications for a patient to the at least one intrinsic component data source or extrinsic component data source; sending a third message to the prescriber through the network linked system if at least one of the one or more prescribed medications is matched with at least one contraindication based on the comparison between the one or more prescribed medications and the at least one intrinsic component data source or extrinsic component data source, and; editing the one or more prescribed medications with any modifications the prescriber may make based on the contraindication, thereby creating one or more revised prescribed medications. The retrospective intervention comprises the steps of recognizing a triggering event; comparing the one or more prescribed medications for a patient to the at least one intrinsic component data source or extrinsic component data source; sending a fourth message though the networked linked system to the prescriber if at least one of the one or more prescribed medications or revised prescribed medications is matched with at least one contraindication based on the comparison between the one or more prescribed medications or revised prescribed medications and the at least one intrinsic component data source or extrinsic component data source; and editing the one or more prescribed medications or revised prescribed medications with any modifications the prescriber may make based on the contraindication, thereby creating one or more revised prescribed medications. The pharmacist dispenses the one or more prescribed medications or the one or more revised prescribed medications after the concurrent intervention or the retrospective intervention.

BRIEF DESCRIPTION OF THE DRAWINGS

The invention will become more readily apparent from the following description of preferred embodiments thereof shown, by way of example only, in the accompanying drawings wherein.

DETAILED DESCRIPTION OF THE INVENTION

Figure 1:
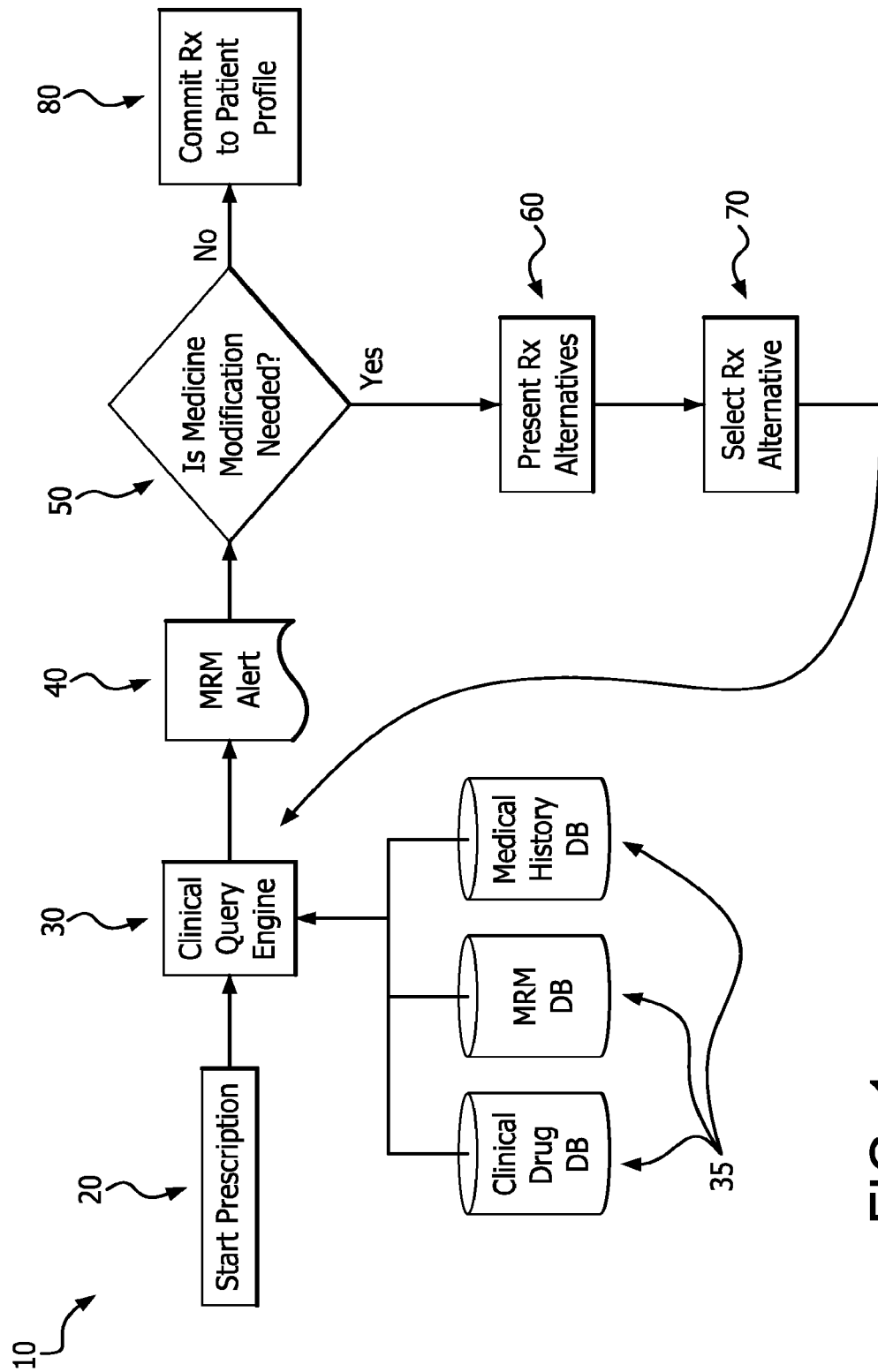
FIG. 1 is a diagram describing a system for carrying out a prospective intervention according to one embodiment of the invention.

The Medication Risk Mitigation (MRM) system of the instant invention applies an array of evidenced-based components and numerous personalized components (e.g., pharmacogenomics, renal function, etc.) to enhance medication safety by individualizing a medication care plan. The system of the instant invention also invokes an assortment of patient-specific interventions to measurably improve medication adherence. The system of the instant invention utilizes a computer program product comprising a non-transitory computer readable medium having program instructions stored in a memory device, the instructions executable by a processor to direct the performance of operations for the management of a regimen for a patient's use of prescribed medication. This MRM process distinctively integrates a medication decision support web/cloud MRM platform with pharmacists and prescribers in order to minimize the pandemic of medication-related morbidity and mortality, while decreasing the rate and alarming cost of medication-induced problems. Advantageously, the instant invention reduces ER visits and hospitalizations, with accompanying improvements in quality of life, medication concordance and adherence. The system of the instant invention is scalable to meet global implementation.

The MRM system of the instant invention provides prospective, concurrent and retrospective interventions, as each are described below.

A. Prospective Intervention

The prospective intervention occurs when a physician, for example, prescribes one or more drugs using an integrated web/cloud system. At the point a physician prescribes a medication, the system of the instant invention automatically presents those intrinsic and extrinsic components that are indicated with each requested medication. Each indicated component is presented for the new medication, along with the aggregated impact for the complete medication profile. Based on the alert output of the system of the instant invention, a prescribing physician is benefited by information permitting the physician to make informed decisions regarding any necessary changes to the prescription.

Once the prescription entry process is completed, the indicated components persist on the medication profile throughout the life of the prescription. The components are dynamic in that new components can be added or updated to the current components and can be incorporated with an automatic, retrospective analysis of the current medication profile.

Data attribution and data stores drive the triggering of the said alerts of the instant invention. The system of the instant invention includes a front-end application for managing various intrinsic and extrinsic components for each medication input into the system. A database of the instant invention assigns attribution to specific medications for both extrinsic and intrinsic components. Such extrinsic and intrinsic components are used as the data sources for triggering the said alerts, along with supplying data to other aspects of the instant invention.

Intrinsic components include, by way of non-limiting example:
 a. Lab test results for an individual patient;
 b. concomitant medications prescribed to an individual patient;
 c. documented medication allergies for a particular patient;
 d. pharmacogenomic data for a particular patient based on medication metabolizing isoenzymes and transporters; and
 e. medication adherence information for an individual patient Next, the system of the instant invention checks for known complications of a particular medication or particular combination of concomitant medications based on the available inputs, along with complications based on extrinsic components which include, but are not limited to:
 a. Beers listed medications;
 b. GCN Sequence Number;
 c. RxCUID (RxNorm);
 d. NDC;
 e. medication name;
 f. START/STOPP criteria;
 g. black-box FDA warnings;
 h. CNS sedative burdens; and
 i. aggregated Anticholinergic Cognitive Burden B. Concurrent Intervention Once a prescriber finishes prescribing the medication, the medication requests are received electronically by a participating pharmacist, via secure instant messaging by way of programmed computers or handheld devices via the internet according to one embodiment of the invention. The participating pharmacist then reviews the patient's medication profile, as well as pertinent lab test results, and applies the instant invention to evaluate the aforementioned extrinsic and intrinsic components. By combining the components with pharmacotherapy best practices, a targeted risk assessment is completed. Potential identified preventable medication-related problems are communicated back to the prescriber using, according to one embodiment of the invention, a secure instant messaging system, including recommendations from the pharmacist to the prescriber.

There are specific utilities for applying the concurrent intervention, even though the same MRM components are applied in each step. A prescriber at the prospective intervention may neglect to apply the components or be uncertain as to the importance of a given component, such as an unfamiliarity with a particular pharmacogenomic contraindication. Advantageously, a concurrent intervention by a pharmacist permits a second review of the same information in order to reduce the likelihood of missing a particular fact. Additionally, a pharmacist may also have specific knowledge of competitive receptor pharmacogenomics that a prescribing physician may lack. In one embodiment, a pharmacist may also have knowledge regarding drugs a patient is taking that may not be known by the prescriber.

Next, the prescriber can optionally respond back to the pharmacist with information that may necessitate a modification of a given prescription based on the aforementioned analysis. This response is made using the same secure instant messaging system, according to one embodiment of the instant invention. In a preferred embodiment, recommendations for medication modifications are accompanied by a structured risk mitigation interface that allows for prescribers to automatically propagate medication changes to a patient's profile upon accepting the recommendations.

C. Retrospective Intervention

The instant invention is also evoked every six months (or upon need or the change or addition of any input into the system, such as a new patient lab result or updated extrinsic component) by a participating pharmacist as he/she performs a semi-annual comprehensive medication review. This triggers a report containing MRM recommendations to the prescriber via the instant invention's secure instant messaging system, according to one embodiment. Recommendations can include medication dosage modifications, medication substitution recommendations and cessation of medication. Recommendations are based on the instant invention's aforementioned application of extrinsic and intrinsic components—whereby all of which may be updated dynamically using the instant invention as new patient tests are performed or new medical information becomes available, for example. Such additional data includes, among other things, adherence and concordance information, medication overutilization calculators and lab values to assess an overall hospitalization, fall or other medication misadventuring risk to a patient at a given point in time. Upon reviewing and accepting the recommended MRM strategies, prescribers can manually (and, in a preferred embodiment, automatically by way of the aforementioned structured risk mitigation interface) propagate medication changes and monitoring parameters for tracking, trending and reporting purposes against the established targeted outcomes (namely, reductions in hospitalizations, falls and medication misadventures).

In another embodiment, the system of the instant invention provides prescribers and pharmacists with an application that allows for the analysis of a prospective medication regimen change in the form of either a new or a replacement therapy. This analysis demonstrates the projected impact of proposed medication changes against the current risk profile of the patient's medication regimen in the context of the extrinsic and intrinsic components. Predictive modeling is based on the weighted correlation of the targeted outcomes (i.e. reductions in hospitalizations, falls and medication misadventuring) against various medication and patient characteristics (both intrinsic and extrinsic).

In one embodiment of the instant invention, a plurality of pharmacists and/or a plurality of prescribers all treating the same patient all share access to the system of the instant invention by means of access to a cloud-based computer system.

By way of further illustration, the system of the instant invention aggregates and presents the various alerts based on the aforementioned triggers. The pharmacist interprets the array of results, using other patient-specific parameters (e.g., kidney function trend, liver function trend, age, medication use history and incidence of Adverse Medication Events, etc.), and provides educated guidance on medication therapy regimen choices in the form of a human generated report.

Turning to the figures, there is shown in FIG. 1 a diagram of the prospective intervention process, generally indicated by reference numeral 10. At step 20, a prescription is made by a prescribing physician (or other health care provider licensed to write prescriptions) participating in the system of the instant invention. The prescription is transmitted via a computer network to a clinical query engine 30. The clinical query engine 30 receives input from one or more databases 35. In a preferred embodiment, the databases 35 include information containing information on clinical drugs, a storage database for records generated through the system of the instant invention, medical records for individual patients, including prescriptions, lab results and patient records, along with any medical histories for patients that may come from third parties. The databases 35 include all of the extrinsic and intrinsic data that are collected pursuant to the instant invention.

Based on any of the above-mentioned indications or contraindications, one or more alerts 40 may be issued. Based on the alert 40, the prescriber may consider whether it is necessary to make a modification to his or her prescription at step 50. If a modification is determined by the prescriber to be necessary, the system of the instant invention presents prescription alternatives that are known in the art at step 60 which, when selected by the prescriber according to the computer drive process of the instant invention at step 70, the process returns to consider the new medicine selection with the clinical query engine 30 and proceeds thereafter in the manner herein described.

Had the prescriber elected to bypass step 50 or in the circumstance where there was no alert 40 or step 50, then the system of the instant invention would commit the medication to a patient's profile 80 (which would be stored in a database 35).

Figure 2:
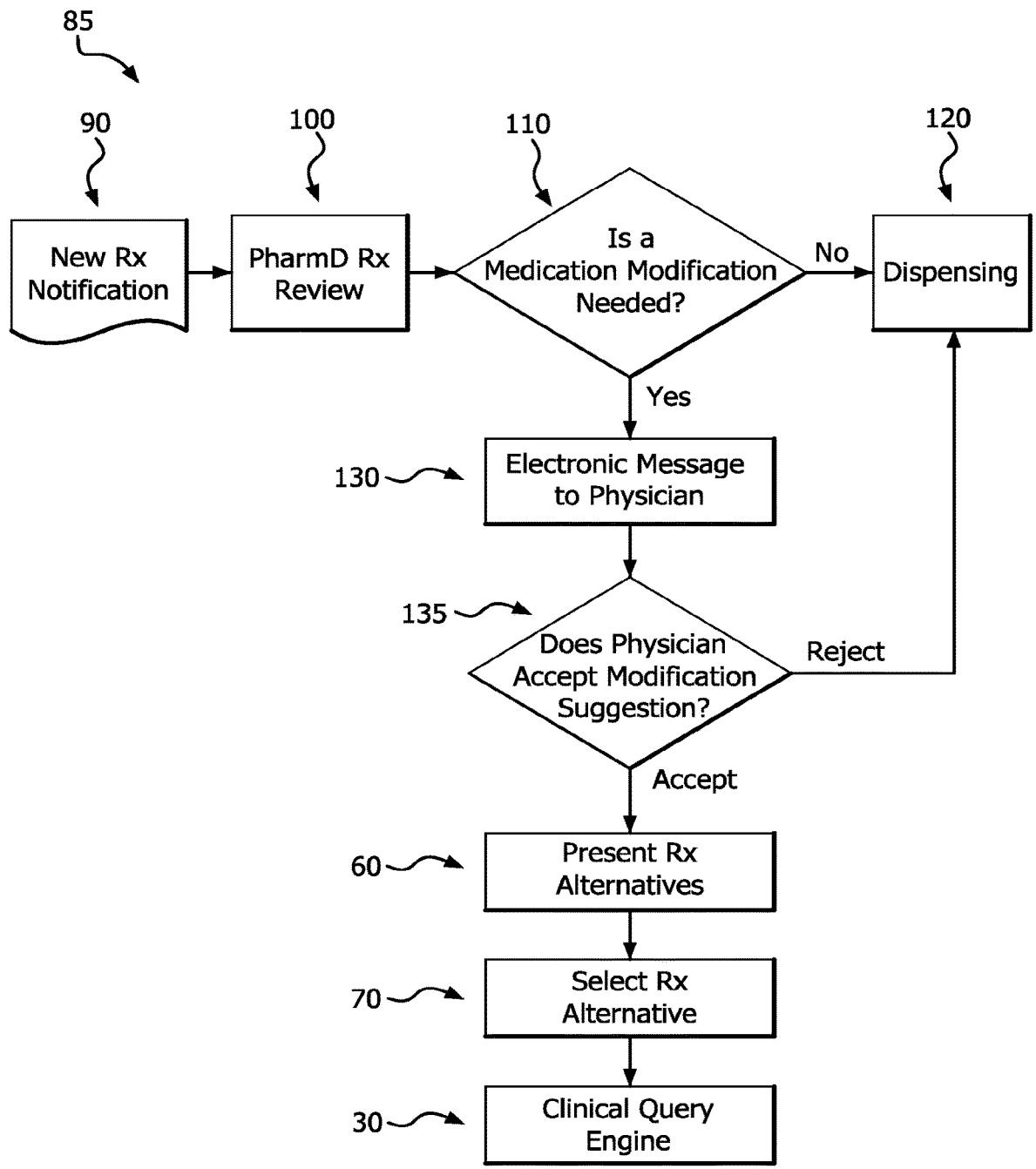
FIG. 2 is a diagram describing a system for carrying out a concurrent intervention according to one embodiment of the invention.

Turning to the concurrent intervention process depicted in FIG. 2 and generally identified by reference number 85, once the medication is committed to a patient's profile 80 (as depicted in FIG. 1), the system of the instant invention generates a computer delivered notification 90 that alerts a pharmacist using the system of the instant invention of a pending new prescription. At this point, the concurrent review begins.

A pharmacist reviews the prescription at step 100. The pharmacist reviews any alerts 40 that are generated by the clinical query engine 30 and also applies his or her knowledge of pharmacotherapy best practices 100 in order to facilitate his or her review of the prescription. Based on the pharmacist's review, he or she must determine whether or not to request a medication change from the prescriber at step 110. If no change is needed, the pharmacist will submit the prescription to the pharmacy to be dispensed at step 120. However, if the pharmacist desires to request a medication modification, the system of the instant invention provides a secure computer facilitated electronic message from the pharmacist to the prescriber at step 130. The computer facilitated electronic message may take the form of a user-generated message or, in an alternative embodiment, it may take the form of a computer form with system generated fields for messages to be standardized according to industry practice. The prescriber then considers whether to accept or reject the suggested medication recommendation(s) at step 135. Upon reviewing the recommendations generated at step 130, a prescriber may reject the proposed medication modification, in which case the process proceeds to step 120. Alternatively, if the prescription is modified, then the system reverts to step 60 from FIG. 1 (which is reproduced in FIG. 2) where the system of the instant invention presents alternative prescription options that a prescriber selects at step 70 from FIG. 1 (which is reproduced in FIG. 2), which loops the system back to the clinical query engine 30 from FIG. 1 (which is reproduced in FIG. 2) and the process continues accordingly, as depicted in FIG. 1.

Figure 3:
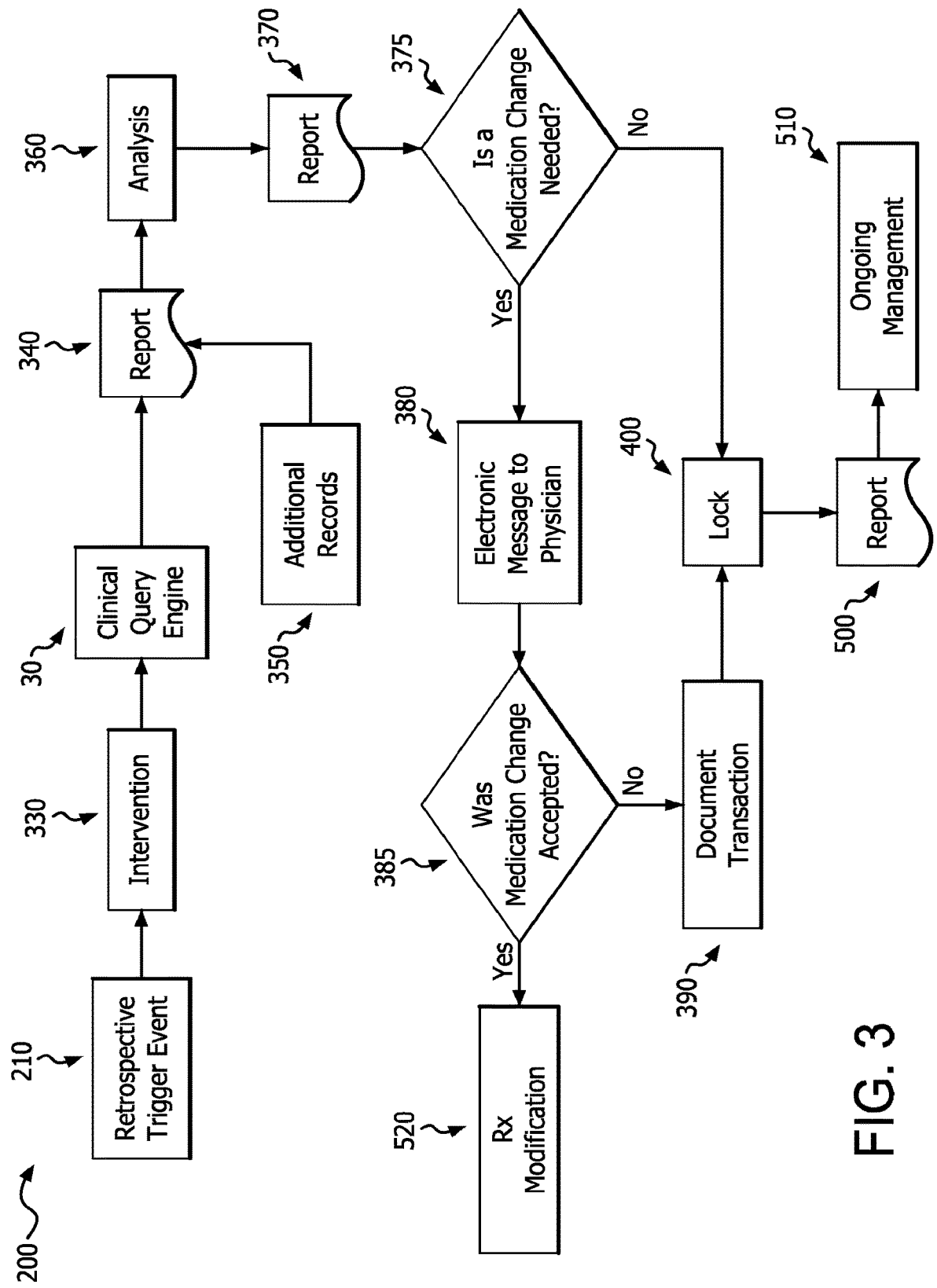
FIG. 3 is a diagram describing a system for carrying out a retrospective intervention according to one embodiment of the invention.

Turning now to FIG. 3, there is shown a diagram of the retrospective review, generally indicated by reference numeral 200. This process begins when a new patient is admitted to a health care facility utilizing the system of the instant invention, automatically every six months, or upon request based on a fall, recent hospitalization or otherwise, as shown in step 210. Once one of the aforementioned triggering conditions is met, an intervention is initiated at step 330. The system of the instant invention utilizes the clinical query engine 30 (depicted in FIG. 1) in order to produce a computer generated report at step 340. Here, additional records 350 contain data that may have been added over time to one of the databases 35 (depicted in FIG. 1). Such records 350 may contain clinical analytics and calculators, MRM components (such as the intrinsic and extrinsic components listed above), medication adherence and concordance analysis, lab results and intrinsic assessments, along with written records reflecting pharmacotherapy best practices. Over time, certain trends in lab results, for example, may present opportunities for medication modification that were not apparent at the prospective or concurrent stages.

Based on this review, a pharmacist may recommend medication changes, identify monitoring parameters, establish clinical milestones or predict outcomes and risks. Each such action is recorded in a databases 35 (as shown in FIG. 1) of the system of the instant invention at step 360. The pharmacist then prepares a report 370 which is recorded in a databases 35 (as shown in FIG. 1) of the system of the instant invention, which may include a medication change request determination at step 375. If a medication change request is made, a secure message (of the type previously discussed) is sent to the participating prescriber at step 380. Here, the prescriber can decide at step 385 whether to accept or reject to the proposed modification by following the procedure beginning at step 135 in FIG. 2. If the recommendation is rejected, then the system of the instant invention documents the transaction and reverts to the previous medical regimen parameters at step 390. Afterwards, the system of the instant invention locks the monitoring parameters and the targeted outcomes at step 400. At step 400, the system of the instant invention permits visibility into metrics in order to determine whether anticipated benefits from previous changes were actually realized. For example, a prescription could be modified to reduce cognitive burdens and reduce the frequency of falls. The system of the instant invention, therefore, permits the frequency of falls to be tracked over time after the said modification was made in order to determine whether it was effective in achieving the desired ends.

These results are displayed by the system of the instant invention in the form of a pharmacist's system generated report at step 500. In turn, ongoing medication management occurs at step 510 until the next trigger event 210 occurs.

However, if the prescriber decided at step 385 to accept a proposed medication modification, then the system of the instant invention would present the prescriber with the opportunity to make a medication modification in the manner herein previously described, as shown at step 520. Once a modification is made, the system of the instant invention reverts to the instantiation of the clinical query engine 30 in FIG. 1 and proceeds thereafter in the manner described herein. Furthermore, if a pharmacist decided that a medication change was not recommended at step 375, then the system of the instant invention would proceed to step 400.

Figure 4:
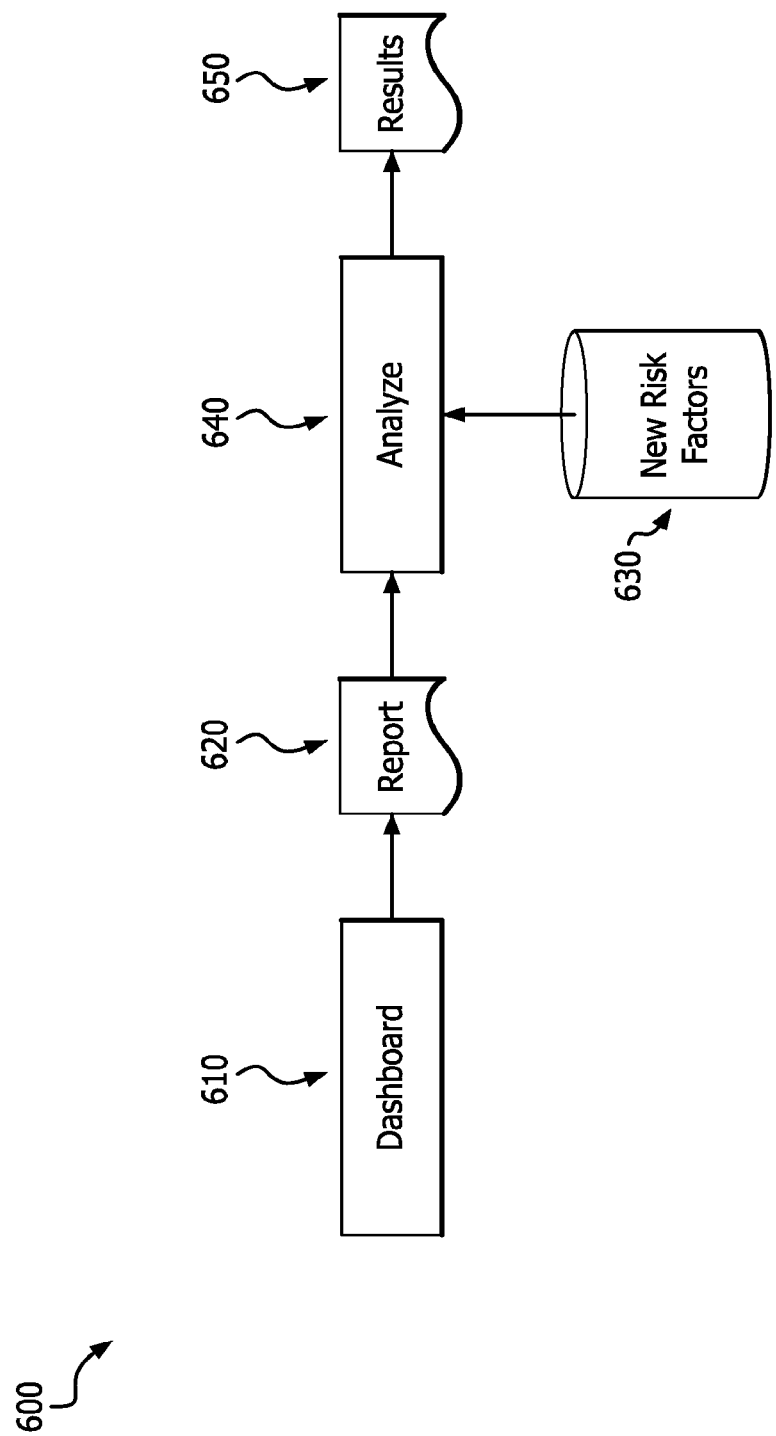
FIG. 4 is a diagram describing a system for carrying out a decision support and predictive clinical outcome component according to one embodiment of the invention.

FIG. 4 depicts the decision support and predictive clinical outcomes component of the instant invention, as generally identified by reference numeral 600. A physician or pharmacist may use the system of the instant invention to view a MRM dashboard 610. Here, a report 620 for a given patient can be reviewed in order to visualize risk profiles and weighted risk factors. Weighted risk profiles include each of the aggregated risk factors, number of medications being taken concurrently, duration of therapy of the existing medications, drug allergies, patient demographics, documented lab results and lab results trending (e.g. INR, CrCl, BMI, etc.). Risk factors incorporated into the weighted risk profiles include aACB score, Sedative burden, drug metabolism pathway, drug-drug interactions, drug-gene interactions and published drug guidelines (e.g. Beers List, FDA Black Box warnings).

For example, the system of the instant invention permits an operator to input additional personalized risk factors into the system of the instant invention at step 630 which are then analyzed using the system of the instant invention at step 640 as data is captured and the volume of clinical information grows, the risk profile and weighted risk factors are refined due to the model establishing greater correlation between targeted outcomes and patient markers (e.g. demographic characteristics, intrinsic attributes, current medications). Based on this analysis, it is possible to hypothetically model the impact of proposed medication modifications using the system of the instant invention with report 650. If any changes to the medication profile are warranted, then they may be implemented in the manner herein previously described.

What is claimed is:

1. A method for generating a report for medication risk mitigation (MRM), the method comprising:

A network linked computer program product comprising a non-transitory computer readable medium having program instructions stored in a memory device, the instructions executable by a processor to direct the performance of operations for the management of a regimen for a patient's use of prescribed medication, the program instructions comprising the steps of:

initializing a prospective intervention comprising the steps of:

receiving at least one medication input from a prescriber for the patient into the memory device;

comparing the at least one medication input for the patient to at least one intrinsic component data source and/or extrinsic component data source, wherein the at least one intrinsic component data source and/or extrinsic component data source includes one or more weighted risk factors;

selecting another medication when the at least one medication input is linked with a contraindication based on the at least one intrinsic component data source and/or extrinsic component data source, including the weighted risk factors;

sending a first message including the another medication to the prescriber through the network linked computer program if the at least one medication input is matched with at least one contraindication based on the comparison between the at least one medication input and the at least one intrinsic component data source and/or extrinsic component data source;

editing the at least one medication input with any modifications the prescriber may make based on the contraindication, thereby creating one or more prescribed medications;

initializing a concurrent intervention comprising the steps of:

sending a second message to a pharmacist device through the network linked computer program comprising the one or more prescribed medications;

comparing, at the pharmacist device, the one or more prescribed medications for the patient to the at least one intrinsic component data source and/or extrinsic component data source;

selecting another medication when the prescribed medication is linked with a contraindication based on the at least one intrinsic component data source and/or extrinsic component data source, including the weighted risk factors;

sending, at the pharmacist device, a third message including the another medication to the prescriber through the network linked computer program if at least one of the one or more prescribed medications is matched with at least one contraindication based on the comparison between the one or more prescribed medications and the at least one intrinsic component data source and/or extrinsic component data source;
editing the one or more prescribed medications with any modifications the prescriber may make based on the contraindication, thereby creating one or more revised prescribed medications;
initializing a retrospective intervention comprising the steps of:
recognizing a triggering event;
comparing the one or more prescribed medications and/or revised prescribed medications for a patient to the at least one intrinsic component data source and/or extrinsic component data source;
selecting another medication when the prescribed medication is linked with a contraindication based on the at least one intrinsic component data source and/or extrinsic component data source, including the weighted risk factors;
sending a fourth message including the another medication though the networked linked computer program to the prescriber if at least one of the one or more prescribed medications or revised prescribed medications is matched with at least one contraindication based on the comparison between the one or more prescribed medications or revised prescribed medications and the at least one intrinsic component data source and/or extrinsic component data source; and
editing the one or more prescribed medications or revised prescribed medications with any modifications the prescriber may make based on the contraindication, thereby creating one or more revised prescribed medications;
generating an output MRM report comprising a visualized representation of weighted risk profiles, weighted risk factors, and a list of options for medication dosage modification, medication substitution and/or medication cessation; and
the pharmacist dispensing the one or more prescribed medications after the concurrent intervention and/or the retrospective intervention,
wherein the weighted risk factors include:
Food and Drug Administration (FDA) adverse event reporting data,
Anticholinergic Cognitive Burden (ACB),
sedative burden for a particular drug,
drug metabolism pathway,
drug-drug interactions,
drug-gene interactions,
wherein the weighted risk profiles include:
each of the aggregated weighted risk factors,
the number of medications being taken concurrently,
duration of therapy of the existing medications,
Anticholinergic Cognitive Burden Index
Creatine Clearance,
interaction warnings;
wherein the intrinsic component data source comprises:
lab test results for an individual patient;
concomitant medications prescribed to an individual patient;
documented medication allergies for a particular patient;
pharmacogenomics data for a particular medication(s) based on medication metabolizing isoenzymes and transporters and their impact; and
medication adherence information for an individual patient; and
wherein the extrinsic component data source comprises:
Beers listed medications;
medication name;
START/STOPP criteria;
FDA adverse event reporting data;
Drug metabolism data;
Extent of drug metabolism pathways data;
black-box Food and Drug Administration warnings;
central nervous system (CNS) sedative burdens; and
aggregated Anticholinergic Burden.

2. The method of claim 1, wherein the intrinsic component data source and/or the extrinsic component data source are updated dynamically as new information becomes available.

3. The method claim 2, wherein the triggering event occurs when the intrinsic component data source and/or the extrinsic component data source are updated.

4. The method claim 1, wherein the triggering event occurs: (i) every six months after the prospective intervention, (ii) after the patient falls, and/or (iii) after the patient's hospitalization.

* * * * *